（12）United States Patent
Hess et al.

(10) Patent No.: US 11,071,576 B2
(45) Date of Patent: Jul. 27, 2021

(54) FLEXIBLE GUIDE WIRE WITH TANTALUM MARKER

(71) Applicant: Spinal Simplicity, LLC, Overland Park, KS (US)

(72) Inventors: Harold Hess, Leawood, KS (US); Melissa Frock, Larwill, IN (US); Douglas Snell, Overland Park, KS (US); Todd Moseley, Olathe, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 375 days.

(21) Appl. No.: 15/336,377

(22) Filed: Oct. 27, 2016

(65) Prior Publication Data
US 2017/0113024 A1 Apr. 27, 2017

Related U.S. Application Data

(60) Provisional application No. 62/247,011, filed on Oct. 27, 2015, provisional application No. 62/247,020, filed on Oct. 27, 2015.

(51) Int. Cl.
A61B 17/88 (2006.01)
A61M 25/09 (2006.01)
A61B 90/00 (2016.01)
A61B 17/70 (2006.01)
A61M 25/00 (2006.01)
A61M 25/01 (2006.01)
A61B 17/16 (2006.01)

(52) U.S. Cl.
CPC ...... *A61B 17/8897* (2013.01); *A61B 17/1631* (2013.01); *A61B 17/7074* (2013.01); *A61B 17/7091* (2013.01); *A61B 17/8875* (2013.01); *A61B 2090/3966* (2016.02); *A61B 2090/3983* (2016.02); *A61M 25/0053* (2013.01); *A61M 25/0108* (2013.01); *A61M 25/09* (2013.01); *A61M 2025/09133* (2013.01); *A61M 2025/09166* (2013.01)

(58) Field of Classification Search
CPC ....... A61B 17/8897; A61B 2090/3966; A61M 25/09; A61M 2025/09133; A61M 2025/09166; A61M 25/0108
See application file for complete search history.

(56) References Cited

U.S. PATENT DOCUMENTS 4,368,730 A * 1/1983 Sharrock ............... A61M 25/00 27/24.1
4,815,478 A * 3/1989 Buchbinder ...... A61M 25/0136 600/434
4,971,490 A * 11/1990 Hawkins ............... A61M 25/09 600/434

(Continued)

*Primary Examiner* — Sean P Dougherty
(74) *Attorney, Agent, or Firm* — Erise IP, P.A.

(57) ABSTRACT

A guide wire comprises a longitudinal body having a proximal end portion and an opposing distal end portion. The proximal and distal end portions have rigid shafts with a flexible portion disposed therebetween. The flexible portion is fixedly attached to the proximal end portion and distal end portion. An outer surface of the flexible portion has a diameter equal to an outer surface of the proximal end portion and an outer surface of the distal end portion. The distal end portion further comprises at least one marker disposed therein configured to locate a distal tip of the guide wire during imaging.

22 Claims, 3 Drawing Sheets

(56) References Cited

U.S. PATENT DOCUMENTS

| | | | | |
|---|---|---|---|---|
| 5,154,705 A | * | 10/1992 | Fleischhacker | A61B 17/3207<br>600/585 |
| 5,253,653 A | * | 10/1993 | Daigle | A61M 25/09<br>600/434 |
| 5,308,324 A | * | 5/1994 | Hammerslag | A61M 25/0144<br>600/585 |
| 5,480,382 A | * | 1/1996 | Hammerslag | A61M 25/0053<br>600/585 |
| 5,488,761 A | * | 2/1996 | Leone | A61B 17/164<br>29/2.1 |
| 5,497,783 A | * | 3/1996 | Urick | A61B 6/12<br>600/434 |
| 5,683,451 A | * | 11/1997 | Lenker | A61F 2/07<br>606/198 |
| 5,746,701 A | * | 5/1998 | Noone | A61M 25/09<br>600/585 |
| 6,328,702 B1 | * | 12/2001 | Cornelius | A61M 25/0905<br>600/585 |
| 6,356,790 B1 | * | 3/2002 | Maguire | A61B 5/0422<br>607/102 |
| 6,371,943 B1 | * | 4/2002 | Racz | A61M 25/065<br>604/264 |
| 6,428,489 B1 | * | 8/2002 | Jacobsen | A61M 25/0054<br>600/585 |
| 6,458,137 B1 | * | 10/2002 | Klint | A61B 17/12022<br>606/108 |
| 6,682,493 B2 | * | 1/2004 | Mirigian | A61M 25/09<br>600/585 |
| 7,406,775 B2 | * | 8/2008 | Funk | A61F 2/4405<br>33/512 |
| 7,713,215 B2 | * | 5/2010 | Shriver | A61B 17/00234<br>600/585 |
| 8,932,141 B2 | * | 1/2015 | Liebing | F16C 1/06<br>464/52 |
| 8,961,522 B2 | * | 2/2015 | Metzinger | A61B 17/7208<br>606/62 |
| 9,254,143 B2 | * | 2/2016 | Huynh | A61B 17/320758 |
| 9,358,370 B2 | * | 6/2016 | Stiger | A61M 25/09 |
| 9,375,189 B1 | * | 6/2016 | Alsahhaf | A61B 90/39 |
| 9,566,418 B2 | * | 2/2017 | Von Malmborg | A61B 5/0215 |
| 9,848,930 B2 | * | 12/2017 | Huebner | A61B 17/864 |
| 9,949,646 B2 | * | 4/2018 | Belleville | A61M 25/09 |
| 2002/0013540 A1 | * | 1/2002 | Jacobsen | A61M 25/09<br>600/585 |
| 2002/0038129 A1 | * | 3/2002 | Peters | A61B 17/32002<br>606/167 |
| 2003/0120148 A1 | * | 6/2003 | Pacetti | A61M 25/09<br>600/421 |
| 2005/0137501 A1 | * | 6/2005 | Euteneuer | A61M 25/0054<br>600/585 |
| 2006/0293663 A1 | * | 12/2006 | Walkenhorst | A61B 17/7064<br>606/257 |
| 2007/0118053 A1 | * | 5/2007 | Melsheimer | A61M 25/09<br>600/585 |
| 2008/0194991 A1 | * | 8/2008 | Teague | A61M 25/09<br>600/585 |
| 2008/0269641 A1 | * | 10/2008 | O'Shaughnessy | A61F 2/86<br>600/585 |
| 2009/0036768 A1 | * | 2/2009 | Seehusen | A61L 29/106<br>600/424 |
| 2009/0131948 A1 | * | 5/2009 | Liu | A61B 17/8811<br>606/93 |
| 2009/0162531 A1 | * | 6/2009 | Nesbitt | A61L 31/18<br>427/2.12 |
| 2009/0181156 A1 | * | 7/2009 | Nesbitt | A61L 31/10<br>427/2.1 |
| 2009/0211909 A1 | * | 8/2009 | Nesbitt | A61L 31/18<br>204/487 |
| 2010/0049084 A1 | * | 2/2010 | Nock | A61B 90/39<br>600/562 |
| 2010/0049085 A1 | * | 2/2010 | Nock | A61B 90/39<br>600/562 |
| 2011/0040371 A1 | * | 2/2011 | Hanssen | A61F 2/88<br>623/1.22 |
| 2011/0060365 A1 | * | 3/2011 | Felix | A61B 17/7002<br>606/246 |
| 2011/0112527 A1 | * | 5/2011 | Hamilton, Jr. | A61B 17/3468<br>606/41 |
| 2011/0160558 A1 | * | 6/2011 | Rassatt | A61N 1/05<br>600/377 |
| 2012/0089141 A1 | * | 4/2012 | Lee | A61B 18/1477<br>606/41 |
| 2012/0323327 A1 | * | 12/2012 | McAfee | A61F 2/4611<br>623/17.16 |
| 2013/0237963 A1 | * | 9/2013 | Stiger | C23F 4/00<br>604/529 |
| 2013/0324926 A1 | * | 12/2013 | Nelson | A61F 2/04<br>604/115 |
| 2013/0345498 A1 | * | 12/2013 | Pacetti | A61F 2/915<br>600/36 |
| 2014/0018816 A1 | * | 1/2014 | Fenn | A61B 17/8875<br>606/104 |
| 2014/0277097 A1 | * | 9/2014 | Castleberry | A61B 17/12145<br>606/200 |
| 2015/0165170 A1 | * | 6/2015 | Beasley | A61M 25/104<br>604/103.1 |
| 2015/0202011 A1 | * | 7/2015 | Gowda | A61B 17/3423<br>606/130 |
| 2015/0265167 A1 | * | 9/2015 | McGowan | A61B 5/0084<br>600/478 |
| 2016/0074131 A1 | * | 3/2016 | Lubinski | A61B 90/39<br>600/431 |
| 2016/0296293 A1 | * | 10/2016 | Gill | A61B 34/30 |
| 2016/0331443 A1 | * | 11/2016 | Phan | A61B 18/1477 |
| 2017/0055818 A1 | * | 3/2017 | Kermani | A61B 1/233 |
| 2019/0038295 A1 | * | 2/2019 | Omohundro | A61B 17/1633 |
| 2019/0247102 A1 | * | 8/2019 | Biedermann | A61B 90/39 |

* cited by examiner

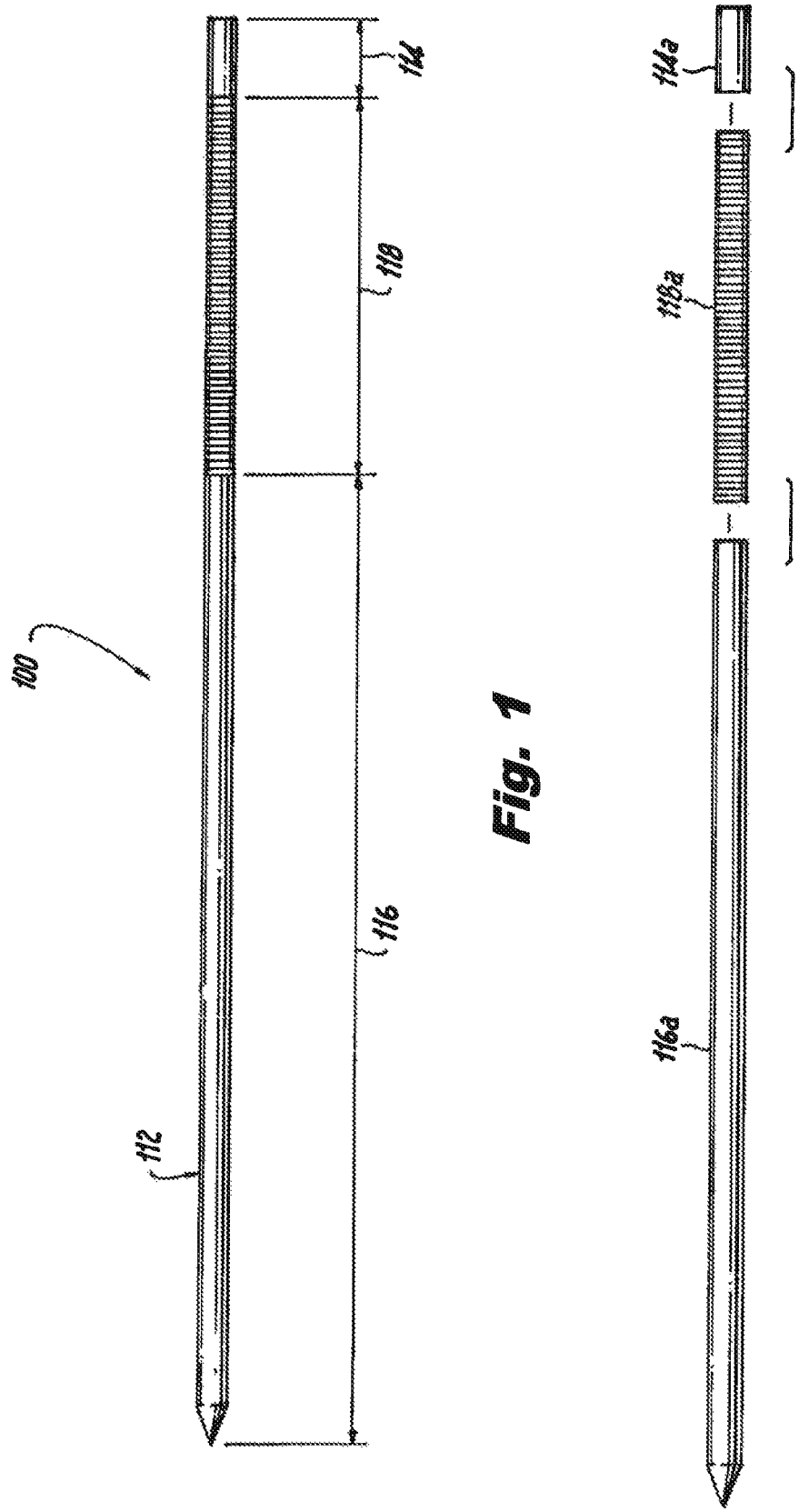

FLEXIBLE GUIDE WIRE WITH TANTALUM MARKER

CROSS-REFERENCE TO RELATED APPLICATION

The subject invention claims the benefit of and priority to U.S. Provisional Patent Application Ser. No. 62/247,011 filed Oct. 27, 2015 and U.S. Provisional Patent Application Ser. No. 62/247,020 filed Oct. 27, 2015, the disclosures of which are herein incorporated by reference in their entirety.

BACKGROUND OF THE INVENTION

1. Field of the Invention

The subject invention is directed to a medical device, and more particularly, to a guidewire for spinal fixation.

2. Description of Related Art

The human spinal column consists of a series of thirty-three stacked vertebrae. Through injury or disease, one or more components of a vertebra become damaged thereby necessitating spinal procedures to remove or modify the damaged component. One way to stabilize the spinal column after such procedures is through spinal fixation.

A spinal fixation procedure can involve rigidly or dynamically fixing adjacent stacked vertebrae vertically through bone grafting and/or rigid mechanical fixation assemblies. A spinal fixation device used in such a procedure may be a rigid or semi-rigid mechanical support system which is surgically implanted into the vertebral column in order to obtain stabilization of spinal fractures, correction of spinal deformities, or treatment of degenerative spinal disease.

The percutaneous technique used to gain access to the intervertebral disc is well known to those of skill in the art. Generally, this technique can be used to place a guide-wire and cannula under C-arm fluoroscopic guidance. Typically, the surgeon would advance a sufficient length of the guide wire into the surgical site to make contact with the bony structure or soft tissue where the surgeon wishes to perform a surgical procedure. When performing spine surgery, the surgeon generally advances a variety of surgical tools over the guide wire, such as a drill and a tap for creating a threaded hole, and then the surgeon typically advances a cannulated bone screw over the guide wire for attachment to the bony structure or tissue. However, when using a relatively stiff guide wire the guide wire can block a surgeon's field of view because the wire is not easily manipulated.

Further, the guidewire distal tip follows a tortuous or winding path as it is inserted into the subject. The distal tip is flexible to avoid damaging interior walls and/or tissue that the guidewire tip contacts along the winding path. One problem with currently available guidewires concerns the visibility of the guidewire. If the guidewire is fully opaque on a viewing screen, it can hinder viewing. Guidewires that have only an opaque tip do not adequately depict the path on the viewing monitor.

Therefore, there arises a need for a guidewire that is made from a single piece having a flexible portion with a marker to allow the guidewire to follow the tortuous path and having a sufficient column strength to allow manipulation of the guidewire from an external access site and including viewing capabilities.

SUMMARY OF THE INVENTION

The subject invention is directed to a new and useful guide wire that includes a longitudinal body having a proximal end portion and an opposing distal end portion. The proximal and distal end portions have rigid shafts. A flexible portion is disposed between the proximal and distal end portions.

The flexible portion is fixedly attached to the proximal end portion and distal end portion. An outer surface of the flexible portion has a diameter equal to an outer surface of the proximal end portion and an outer surface of the distal end portion. The flexible portion is a coil tube that includes stainless steel.

The proximal portion has a longitudinal dimension shorter than a longitudinal dimension of the distal portion and the flexible portion individually. The flexible portion has a longitudinal dimension shorter than a longitudinal dimension of the distal portion. The flexible portion is approximately five inches. The distal portion is approximately thirteen inches and the proximal portion is approximately one inch. The distal end portion has a distal tip configured for guiding a pedicle screw insertion.

The subject invention is also directed to a guide wire comprising a longitudinal body having a proximal end portion and an opposing distal end portion. The distal end portion having at least one marker disposed therein configured to locate a distal tip of the guide wire during imaging. The at least one marker is a high density biocompatible material placed within the distal end portion of the guide wire. The at least one marker is positioned such that a central portion of the marker is co-linear with a distal tip of the guide wire.

Preferably, the at least one marker is machined into a core of the longitudinal body. In one embodiment, the at least one marker is a straight wire. In another embodiment, the at least one marker is a spherical ball. In yet another embodiment, two markers are positioned within the distal end portion of the guide wire perpendicular to each other forming an X shape when viewed laterally along a length of the guide wire.

These and other features of the guide wire of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein:

FIG. 1 is a side schematic view of an exemplary embodiment of a flexible guide wire constructed in accordance with the present disclosure, showing a flexible portion between a rigid proximal end portion and a rigid distal end portion;

FIG. 2 is an exploded side view of the flexible guide wire of FIG. 1, showing the flexible portion fixedly attached to the proximal and distal end portions;

DETAILED DESCRIPTION OF THE PREFERRED EMBODIMENTS

Figure 3:
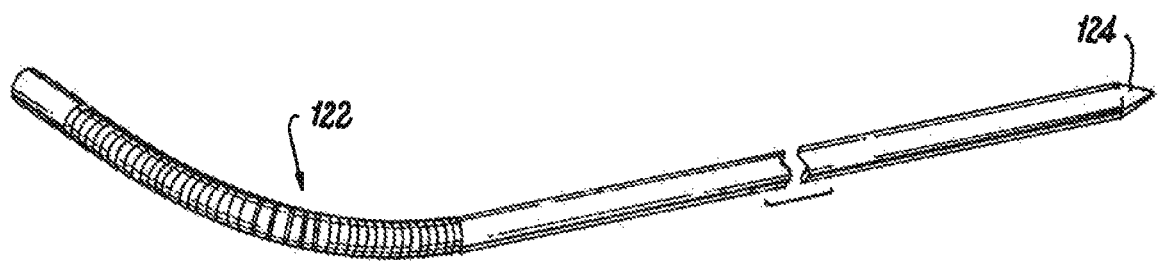
FIG. 3 is a side schematic view of the flexible guide wire, showing a bend in the flexible portion.

Referring now to the drawings wherein like reference numerals identify similar structural features of the claimed invention, there is illustrated in FIG. 1 a flexible guide wire in accordance with a preferred embodiment of the subject invention and designated generally by reference numeral 100. The guide wire 100 is a one-piece longitudinal body 112 configured for use with a C-arm during an operating procedure. The guide wire 100 of the present disclosure has central axis with a proximal end portion 114 and an opposing distal end portion 116 aligned parallel to the central axis. Both the proximal and distal end portions 114, 116 are rigid shafts that provide stability to the guide wire 100.

A flexible portion 118 is positioned between the proximal and distal end portions 114, 116 and fixedly attached thereto. The flexible portion 118 includes a coiled tube formed generally perpendicular to the central axis. The flexible portion 118 allows the guide wire 100 to bend as needed. For example, in some embodiments, the flexible guide wire 100 can be introduced into a surgical site to allow for the introduction of instruments or implants over the flexible guide wire and the surgeon creates an incision in the body to provide access to the surgical site.

In some embodiments, the described method is used to introduce a flexible guide wire to a pedicle of a vertebra to allow for the introduction of a bone drill, bone tap, implant driver, and a threaded spinal implant over the guide wire to the pedicle. It is important to note that such guide wires, including the flexible guide of the present invention, can realistically be used to guide instruments and implants into many locations within the body to allow for a surgeon to complete a surgical procedure. The present disclosure is not meant to limit the use of the flexible guide wire to the disclosed surgical application described herein.

The distal end portion 116 has a larger longitudinal dimension than each of the flexible portion 118 and the proximal portion 114. Preferably, the distal end portion 116 is approximately thirteen inches and the proximal end portion 114 is one inch. The flexible portion 118 includes a stainless steel flexible coil tube that is approximately five inches. Typical guide wires are too long and interfere with the c-arm and therefore need to be moved out of the way. The currently disclosed guidewire 100 is designed so as not to interfere with the c-arm view, however, those skilled in the art will readily appreciate that the length and diameters of each portion may vary depending upon the application.

As shown in FIG. 2, the flexible portion 118, the proximal portion 114 and distal portion 116 align to form one continuous body 112. More specifically, an outer surface 118a of the flexible portion 118 has a diameter equal to a diameter of an outer surface 114a of the proximal portion 114 and an outer surface 116a of the distal portion 116. This provides an easier entry/exit of the guide wire into the incision thereby causing fewer traumas and scarring for the patient. In addition, this provides sufficient column strength to manipulate the guide wire 100. The rigid proximal portion 114 provides a smooth solid end. Further, the flexible portion 118 can be attached to the proximal and distal end portions 114, 116 by welding or the like.

Figure 4:
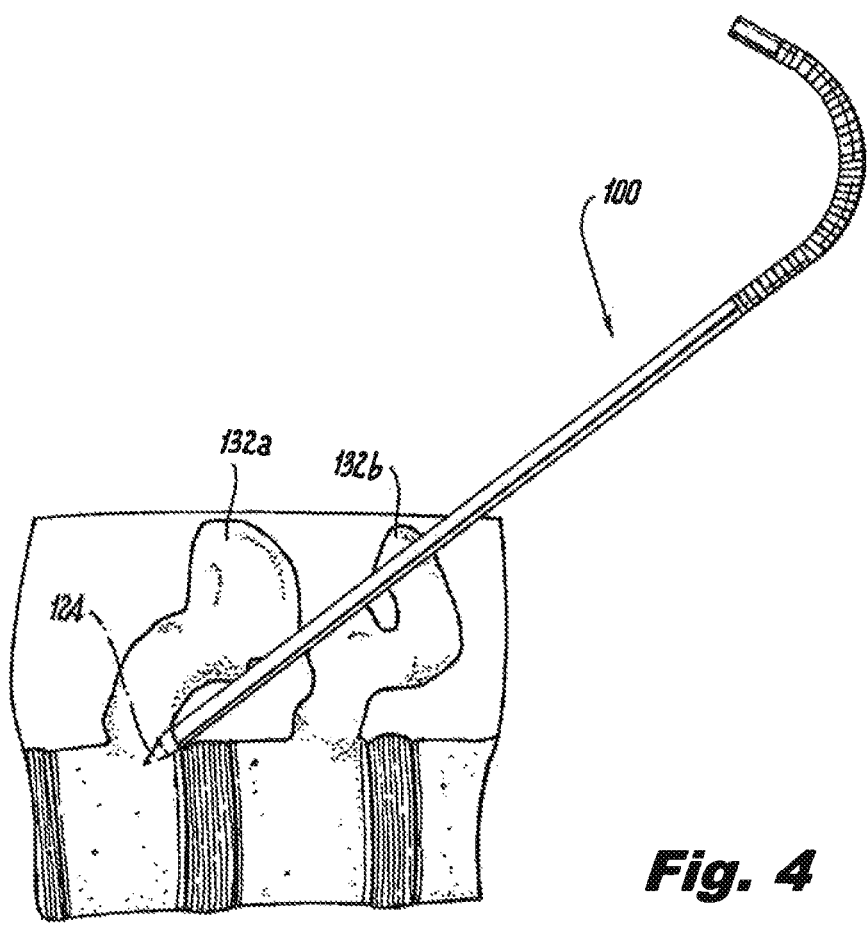
FIG. 4 is a schematic view of the flexible guide wire in use.

With reference to FIGS. 3 and 4, the flexible guide wire 100 is shown with a bend 122 in the flexible portion 118. The coil tube of the flexible portion 118 is biased toward a straight configuration (as shown in FIG. 1), yet sufficiently flexible to navigate an access pathway between vertebrae 132a, 132b (as shown in FIG. 4). FIG. 4 illustrates the flexible guide wire 100 during an operating procedure. The location of insertion of the guide wire 100 is determined by radiographic means (e.g., C-arm flouroscope) and driven until the distal tip 124 reaches the desired location on the surface of a pedicle bone. The distal tip 124 is designed and configured to easily thread through for example, a pedicle screw to achieve accurate placement.

The guide wire 100 of the present disclosure further includes at least one radio-opaque marker 126 placed in the distal end portion 116 near the distal tip 124 to allow a user a clear image of the location of the distal tip 124a. The marker 126 is a tantalum marker(s), including high density biocompatible material. Preferably, the marker 126 is mechanically placed within a generally solid core 112a of the longitudinal body 112 at the distal end portion 116 using standard machining methods. This prevents the marker 126 from interfering with the function and external design of the guide wire 100.

Figures 5, 6:
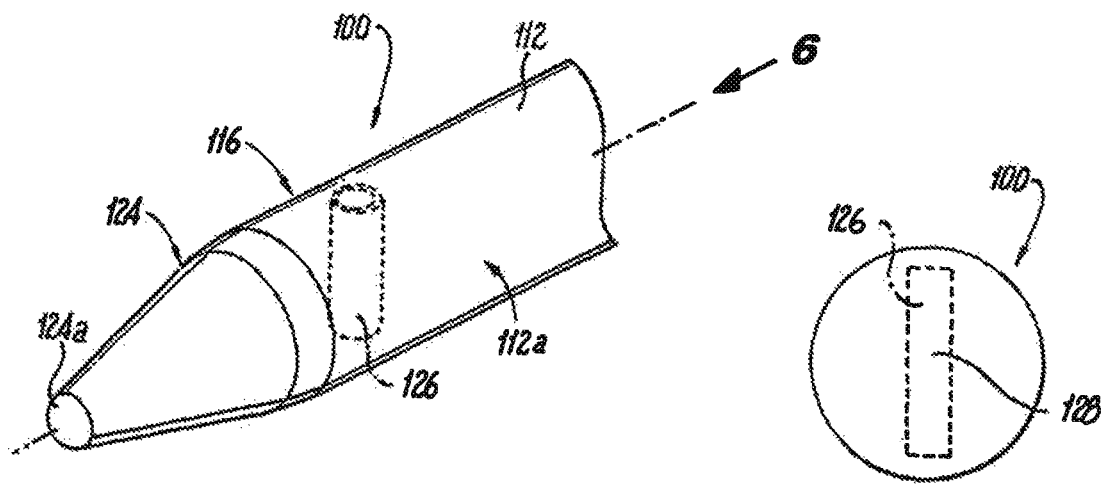
FIG. 5 is a perspective view of a distal end portion of an exemplary embodiment of a guide wire constructed in accordance with the present disclosure, showing a marker in the shape of a cylindrical wire.
FIG. 6 is a top plan view taken in the direction of arrow 6 of the guide wire of FIG. 5.

The marker 126 or markers can be placed in such a way that different configurations or shapes are created when an image is taken from the proximal portion 114. With reference to FIG. 1, the marker 126 is shown as cylindrical rod/wire. Preferably, the marker 126 is positioned such that when the lateral image is taken, the marker 126, best shown in FIG. 6, indicates the location of the distal tip 124a which is aligned with a central portion 128 of the marker 126.

Figures 7, 8:
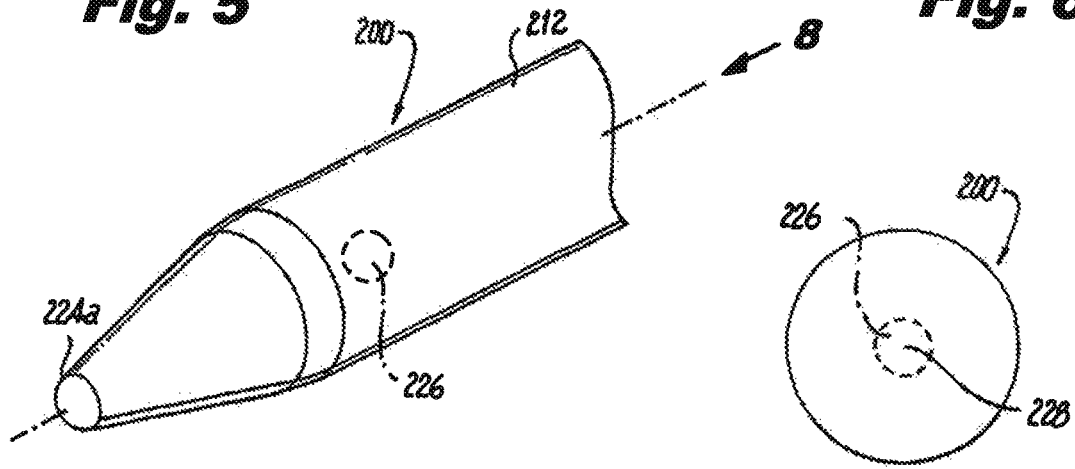
FIG. 7 is a perspective view of a distal end portion of another embodiment of a guide wire constructed in accordance with the present disclosure, showing a marker in the shape of ball.
FIG. 8 is a top plan view of the guide wire taken in the direction of arrow 8 of FIG. 7.

Similarly, as shown in another embodiment of guide wire 200 of FIGS. 7 and 8, the marker 226 can be a spherical ball/bead placed within the longitudinal body 212 of the guide wire 200. The spherical ball 226 is co-linear such that when viewed as a lateral fluoroscopy image a central region 228 (as seen in FIG. 8) of the ball/bead 226 indicates the location of the distal tip 224a.

Figures 9, 10:
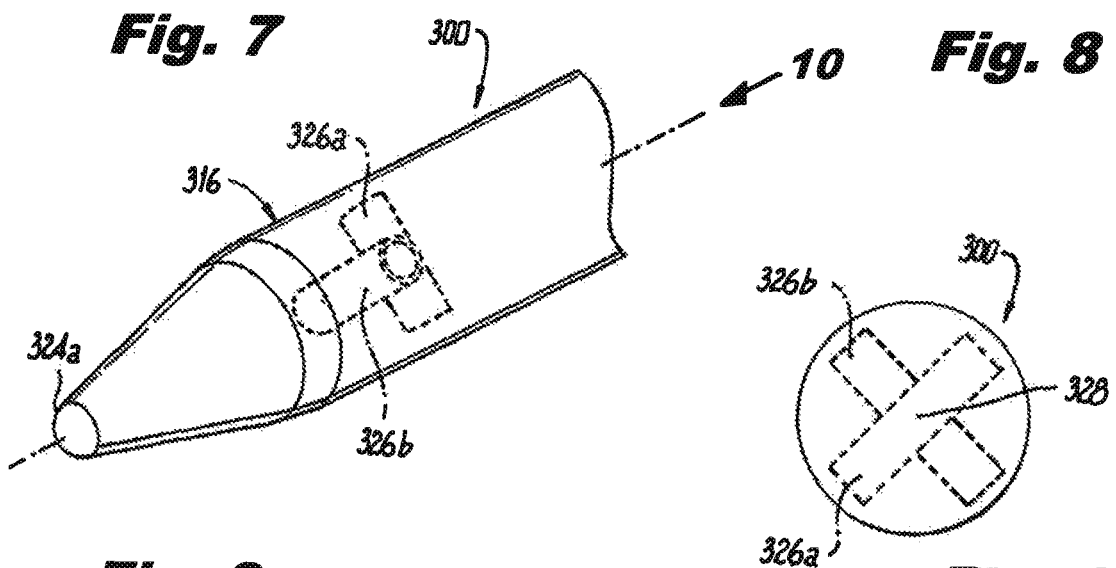
FIG. 9 is a perspective view of a distal end portion of yet another embodiment of a guide wire constructed in accordance with the present disclosure, showing two wire markers perpendicular to each other.
FIG. 10 is a top plan view of the guide wire taken in the direction of arrow 10 of FIG. 9.

With reference to FIGS. 9 and 10, yet another embodiment of a guide wire 300 is shown with two markers 326a, 326b positioned within the distal end portion 316. The markers 326a, 326b are cylindrical rods/wires that are positioned perpendicular to one another. Viewing the guide wire 300 from a lateral fluoroscope illustrates an "X" shape such that the central region 328 indicates the location of the distal tip 324a. The markers 326a, 326b are shown as two rod markers however the use of a plurality of markers is not limited to rod markers. For example, a rod and spherical ball can be used in combination. In another embodiment, multiple spherical balls can be placed in varying configurations to act as markers for taking measurements. Further, markers are not limited to placement within the distal end portion. The markers may be strategically placed throughout the longitudinal body to act as additional guiding features.

While the marker(s) disclosed herein is shown and described for use on a guide wires those skilled in the art will readily appreciate the same can be implemented within spinal needles, temporary pins, or the like in which tip differentiation would be beneficial. Further, while the marker(s) shown and described herein are meant to represent specific shapes, those skilled in the art will readily appreciate that various shapes and configurations can be used to achieve the same results.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. A guide wire configured to be used in a spinal fixation procedure, comprising:
    a longitudinal body having a total length, a central axis, a proximal end, a distal tip, and a flexible portion located between the proximal end and the distal tip;
    a proximal end portion comprising a rigid shaft having a solid core, said proximal end portion extending a first length from the proximal end to the flexible portion; and
    an opposing distal end portion comprising a rigid shaft having a solid core, said distal end portion extending a second length from the distal tip to the flexible portion,
    wherein flexible portion comprises a coiled tube, said flexible portion extending a third length from the proximal end portion to the distal end portion,
    wherein the second length is longer than the first length,
    wherein the second length is longer than the third length,
    wherein the second length is longer than half the total length, and
    wherein the distal end portion comprises at least two intersecting radiopaque markers disposed therein configured to locate the distal tip of the guide wire during imaging.

2. The guide wire of claim 1, wherein the flexible portion is fixedly attached to the proximal end portion and to the distal end portion, and
    wherein an outer surface of the flexible portion has a diameter equal to a diameter of an outer surface of the proximal end portion and a diameter of an outer surface of the distal end portion.

3. The guide wire of claim 1, wherein the flexible portion is formed generally perpendicular to the central axis.

4. The guide wire of claim 1, wherein the flexible portion includes stainless steel.

5. The guide wire of claim 1, wherein the distal end portion is configured for guiding a pedicle screw insertion.

6. The guide wire of claim 1, wherein the first length is less than the third length.

7. The guide wire of claim 1, wherein the third length is approximately five inches.

8. The guide wire of claim 1, wherein the second length is approximately thirteen inches and the first length is approximately one inch.

9. The guide wire of claim 1,
    wherein the at least two markers intersect to form an X shape when viewed laterally along the longitudinal axis of the guide wire indicating an orientation of the distal tip.

10. A guide wire configured to be used in a spinal fixation procedure, comprising:
    a longitudinal body having a longitudinal axis, a proximal end, a distal tip, and a flexible portion located between the proximal end and the distal tip;
    a proximal end portion comprising a rigid shaft having a solid core, said proximal end portion extending a first length from the proximal end to the flexible portion; and
    an opposing distal end portion comprising a rigid shaft having a solid core, said distal end portion extending a second length from the distal tip to the flexible portion,
    the distal end portion having at least one radiopaque marker disposed therein configured to locate the distal tip of the guide wire during imaging,
    said at least one radiopaque marker being machined into the core of the distal end portion of the longitudinal body,
    wherein the at least one radiopaque marker has a longitudinal dimension that is less than the second length, and
    wherein the longitudinal axis of the longitudinal body intersects the at least one radiopaque marker.

11. The guide wire of claim 10, wherein the at least one radiopaque marker is a high density biocompatible material.

12. The guide wire of claim 10, wherein the at least one radiopaque marker is positioned such that a central portion of the marker is co-linearly aligned with the longitudinal axis of the distal tip of the guidewire.

13. The guide wire of claim 10, wherein the at least one radiopaque marker is a straight wire.

14. The guide wire of claim 10, wherein the at least one radiopaque marker is a spherical ball.

15. The guide wire of claim 10, wherein the at least one marker comprises two markers perpendicular to each other.

16. The guide wire of claim 15, wherein the two markers intersect to form an X shape when viewed laterally along the longitudinal axis of the guide wire indicating an orientation of the distal tip.

17. A guide wire configured to be used in a spinal fixation procedure, comprising:
    a longitudinal body having a longitudinal axis, a proximal end, a distal tip, and a flexible portion located between the proximal end and the distal tip;
    a proximal end portion comprising a rigid shaft having a solid core, said proximal end portion extending a first length from the proximal end to the flexible portion; and
    an opposing distal end portion comprising a rigid shaft having a solid core, said distal end portion extending a second length from the distal tip to the flexible portion,
    a flexible portion secured between the proximal end portion and the distal end portion having a third length and an outer surface diameter equal to an outer surface diameter of the proximal end portion and an outer surface diameter of the distal end portion,
    wherein the second length is longer than the first length, and
    wherein the second length is longer than the third length;
    at least two radiopaque markers machined into the core of the distal tip of the longitudinal body and positioned such that a central portion of each marker is co-linearly aligned with the distal tip of the guide wire,
    the at least two radiopaque markers being configured to locate the distal tip of the guide wire during imaging,
    wherein the at least two radiopaque markers intersect to form an X shape when viewed laterally along the longitudinal axis of the guide wire indicating an orientation of the distal tip, wherein the at least one marker has a longitudinal dimension that is less than the second length, and wherein the longitudinal axis of the longitudinal body intersects the at least one marker.

18. A guide wire configured to be used in a spinal fixation procedure, comprising:

a longitudinal body having a central axis, a proximal end, and a distal end;

a flexible portion located between the proximal end and the distal end comprising a coiled tube to allow the guide wire to follow a tortuous path during insertion;

a proximal end portion comprising a rigid shaft having a solid core to provide sufficient column strength to allow manipulation of the guide wire from an external access site, said proximal end portion extending a first length from the proximal end to the flexible portion; and a distal end portion comprising a rigid shaft having a solid core to provide sufficient column strength to allow manipulation of the guide wire from an external access site, said distal end portion extending a second length from the distal end to the flexible portion, at least two radiopaque markers disposed in the distal end portion to locate the distal end of the guide wire during imaging, wherein when viewed laterally along the longitudinal axis of the guide wire, the at least two markers intersect, wherein the flexible portion extends a third length from the proximal end portion to the distal end portion, wherein the second length is longer than the first length, and wherein the second length is longer than the third length.

19. The guide wire of claim 18, wherein the second length is at least twice as long the third length.

20. A guide wire configured to be used in a spinal fixation procedure, comprising:

a longitudinal body having a central axis, a proximal end, and a distal end;

a flexible portion located between the proximal end and the distal end comprising a coiled tube to allow the guide wire to follow a tortuous path during insertion;

a proximal end portion comprising a rigid shaft with a solid core to provide sufficient column strength to allow manipulation of the guide wire from an external access site, said proximal end portion extending a first length from the proximal end to the flexible portion; and a distal end portion comprising a rigid shaft with a solid core to provide sufficient column strength to allow manipulation of the guide wire from an external access site, said distal end portion extending a second length from the distal end to the flexible portion; and at least two radiopaque markers positioned perpendicular to each other within the solid core of the distal end portion to determine the position and orientation of the distal end portion during imaging, wherein the flexible portion extends a third length from the proximal end portion to the distal end portion, wherein the second length is longer than the first length, and wherein the second length is longer than the third length.

21. The guide wire of claim 20, wherein the at least two radiopaque markers comprise rods.

22. The guidewire of claim 20, wherein the at least two radiopaque markers intersect to form an X shape when viewed laterally along the longitudinal axis of the guide wire indicating an orientation of the distal tip.

\* \* \* \* \*